(12) United States Patent
Wiederkehr

(10) Patent No.: US 10,251,685 B2
(45) Date of Patent: Apr. 9, 2019

(54) FLOATING LOCKING INSERT

(71) Applicant: Stryker European Holdings I, LLC, Kalamazoo, MI (US)

(72) Inventor: Andreas Wiederkehr, Biel/Bienne (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 332 days.

(21) Appl. No.: 15/073,235

(22) Filed: Mar. 17, 2016

(65) Prior Publication Data

US 2017/0265914 A1    Sep. 21, 2017

(51) Int. Cl.
  *A61B 17/80* (2006.01)
  *A61B 17/86* (2006.01)
  *A61B 17/70* (2006.01)

(52) U.S. Cl.
  CPC ...... *A61B 17/8047* (2013.01); *A61B 17/7059* (2013.01); *A61B 17/8057* (2013.01); *A61B 17/8695* (2013.01)

(58) Field of Classification Search
  CPC ............ A61B 17/8014; A61B 17/8019; A61B 17/8028; A61B 17/8033; A61B 17/8047
  USPC ................................................ 606/286–292
  See application file for complete search history.

(56) References Cited

U.S. PATENT DOCUMENTS

| | | | |
|---|---|---|---|
| 4,388,921 A | 6/1983 | Sutter et al. | |
| 4,973,332 A | 11/1990 | Kummer | |
| 5,015,248 A | 5/1991 | Burstein et al. | |
| 5,053,036 A | 10/1991 | Perren et al. | |
| 5,066,296 A | 11/1991 | Chapman et al. | |
| 5,151,103 A | 9/1992 | Tepic et al. | |
| 5,486,176 A | 1/1996 | Hildebrand et al. | |
| 5,531,554 A | 7/1996 | Jeanson et al. | |
| 5,531,745 A | 7/1996 | Ray | |
| 5,681,313 A | 10/1997 | Diez | |

(Continued)

FOREIGN PATENT DOCUMENTS

| | | |
|---|---|---|
| DE | 9308944 U1 | 8/1993 |
| DE | 100 39 767 A1 | 7/2001 |

(Continued)

OTHER PUBLICATIONS

Extended European Search Report for Application No. 17000134, dated Aug. 21, 2017.

*Primary Examiner* — Matthew J Lawson
(74) *Attorney, Agent, or Firm* — Lerner, David, Littenberg, Krumholz & Mentlik, LLP

(57) ABSTRACT

An insert for receipt within a plate aperture having an inner wall along the plate aperture includes a body and collar. The body has inner and outer surfaces. The inner surface defines an insert aperture having a longitudinal axis. The collar extends from the outer surface in a first radial direction perpendicular to the longitudinal axis and extends along only a portion of the outer surface in a second radial direction transverse to the first radial direction and the longitudinal axis. The collar defines a first radial distance from the longitudinal axis at a first position of the collar and a second radial distance from the longitudinal axis at a second position of the collar that differs from the first radial distance. A fixation system includes the plate and insert which is receivable within the plate aperture such that the collar contacts and is slideable along the inner wall.

17 Claims, 5 Drawing Sheets

(56) References Cited

U.S. PATENT DOCUMENTS

| | | |
|---|---|---|
| 5,951,558 A | 9/1999 | Fiz |
| 5,954,722 A | 9/1999 | Bono |
| 5,976,141 A | 11/1999 | Haag et al. |
| 6,017,345 A | 1/2000 | Richelsoph |
| 6,129,728 A | 10/2000 | Schumacher et al. |
| 6,193,721 B1 | 2/2001 | Michelson |
| D440,311 S | 4/2001 | Michelson |
| 6,221,073 B1 | 4/2001 | Weiss et al. |
| 6,235,003 B1 | 5/2001 | Dysarz |
| 6,235,033 B1 | 5/2001 | Brace et al. |
| 6,258,089 B1 | 7/2001 | Campbell et al. |
| 6,273,889 B1 | 8/2001 | Richelsoph |
| D449,692 S | 10/2001 | Michelson |
| 6,331,179 B1 | 12/2001 | Freid et al. |
| 6,398,783 B1 | 6/2002 | Michelson |
| 6,416,528 B1 | 7/2002 | Michelson |
| 6,428,542 B1 | 8/2002 | Michelson |
| 6,454,769 B2 | 9/2002 | Wagner et al. |
| 6,454,771 B1 | 9/2002 | Michelson |
| 6,503,250 B2 | 1/2003 | Paul |
| 6,520,965 B2 | 2/2003 | Chervitz et al. |
| 6,527,776 B1 | 3/2003 | Michelson |
| 6,533,786 B1 | 3/2003 | Needham et al. |
| 6,533,789 B1 | 3/2003 | Hall, IV et al. |
| 6,572,622 B1 | 6/2003 | Schafer et al. |
| 6,575,975 B2 | 6/2003 | Brace et al. |
| 6,592,586 B1 | 7/2003 | Michelson |
| 6,602,256 B1 | 8/2003 | Hayes |
| 6,616,666 B1 | 9/2003 | Michelson |
| 6,620,163 B1 | 9/2003 | Michelson |
| 6,626,907 B2 | 9/2003 | Campbell et al. |
| 6,645,209 B2 | 11/2003 | Hall, IV et al. |
| 6,652,525 B1 | 11/2003 | Assaker et al. |
| 6,652,530 B2 | 11/2003 | Ip et al. |
| 6,663,632 B1 | 12/2003 | Frigg |
| 6,669,700 B1 | 12/2003 | Farris et al. |
| 6,679,883 B2 | 1/2004 | Hawkes et al. |
| 6,695,846 B2 | 2/2004 | Richelsoph et al. |
| 6,712,818 B1 | 3/2004 | Michelson |
| 6,730,091 B1 | 5/2004 | Pfefferle et al. |
| 6,755,831 B2 | 6/2004 | Putnam et al. |
| 6,890,334 B2 | 5/2005 | Brace et al. |
| 6,890,335 B2 | 5/2005 | Grabowski et al. |
| 6,916,320 B2 | 7/2005 | Michelson |
| 6,926,718 B1 | 8/2005 | Michelson |
| 6,929,646 B2 | 8/2005 | Gambale |
| 6,936,050 B2 | 8/2005 | Michelson |
| 6,936,051 B2 | 8/2005 | Michelson |
| 6,969,390 B2 | 11/2005 | Michelson |
| 6,984,234 B2 | 1/2006 | Bray |
| 7,001,388 B2 | 2/2006 | Orbay et al. |
| 7,074,221 B2 | 7/2006 | Michelson |
| 7,090,676 B2 | 8/2006 | Huebner et al. |
| 7,137,984 B2 | 11/2006 | Michelson |
| 7,175,623 B2 | 2/2007 | Thramann et al. |
| 7,195,633 B2 | 3/2007 | Medoff et al. |
| 7,229,443 B2 | 6/2007 | Eberlein et al. |
| 7,273,481 B2 | 9/2007 | Lombardo et al. |
| 7,303,564 B2 | 12/2007 | Freid et al. |
| 7,326,212 B2 | 2/2008 | Huebner |
| 7,625,381 B2 | 12/2009 | Michelson |
| 7,682,379 B2 | 3/2010 | Mathieu et al. |
| 7,704,251 B2 | 4/2010 | Huebner et al. |
| 7,704,255 B2 | 4/2010 | Michelson |
| 7,758,620 B2 | 7/2010 | Porcher |
| 7,771,458 B2 | 8/2010 | Biedermann et al. |
| 7,780,710 B2 | 8/2010 | Orbay et al. |
| 7,794,482 B2 | 9/2010 | Mathieu et al. |
| 7,833,254 B2 | 11/2010 | Celli et al. |
| 7,887,569 B2 | 2/2011 | Frigg |
| 7,942,913 B2 | 5/2011 | Ziolo et al. |
| 7,972,366 B2 | 7/2011 | Richelsoph et al. |
| 8,075,602 B2 | 12/2011 | Lombardo et al. |
| 8,147,530 B2 | 4/2012 | Strnad et al. |
| 8,172,885 B2 | 5/2012 | Songer et al. |
| 8,177,819 B2 | 5/2012 | Huebner et al. |
| 8,216,283 B2 | 7/2012 | Mathieu et al. |
| 8,221,421 B2 | 7/2012 | Hearn |
| 8,226,692 B2 | 7/2012 | Mathieu et al. |
| 8,287,575 B2 | 10/2012 | Murner et al. |
| 8,337,534 B2 | 12/2012 | Celli et al. |
| 8,388,665 B2 | 3/2013 | Eberlein et al. |
| 8,398,636 B2 | 3/2013 | Simon et al. |
| 8,439,957 B2 | 5/2013 | Lombardo et al. |
| 8,444,680 B2 | 5/2013 | Dooney, Jr. et al. |
| 8,486,116 B2 | 7/2013 | Heilman |
| 8,486,118 B2 | 7/2013 | Mathieu et al. |
| 8,500,737 B2 | 8/2013 | Richelsoph et al. |
| 8,518,042 B2 | 8/2013 | Winslow et al. |
| 8,579,898 B2 | 11/2013 | Prandi et al. |
| 8,652,179 B2 | 2/2014 | Graham et al. |
| 8,668,723 B2 | 3/2014 | Altarac et al. |
| 8,728,129 B2 | 5/2014 | Fritzinger et al. |
| 8,734,494 B2 | 5/2014 | Simon et al. |
| 8,828,064 B2 | 9/2014 | Ziolo et al. |
| 8,906,070 B2 | 12/2014 | Medoff |
| 8,961,573 B2 | 2/2015 | Gonzalez-Hernandez |
| 8,998,904 B2 | 4/2015 | Zeetser et al. |
| 9,072,557 B2 | 7/2015 | Fierlbeck et al. |
| 9,084,636 B2 | 7/2015 | Mekhail et al. |
| D735,861 S | 8/2015 | Embleton et al. |
| 9,131,968 B2 | 9/2015 | Cavallazzi et al. |
| 9,138,244 B2 | 9/2015 | Mebarak et al. |
| 9,138,267 B2 | 9/2015 | Cavallazzi |
| 9,155,577 B2 | 10/2015 | Pfefferle et al. |
| 9,241,749 B2 | 1/2016 | Lombardo et al. |
| 9,254,154 B2 | 2/2016 | Gonzalez-Hernandez |
| 9,308,033 B2 | 4/2016 | Huebner et al. |
| 9,333,014 B2 | 5/2016 | Gonzalez-Hernandez |
| 9,522,066 B2 | 12/2016 | Segina et al. |
| 2002/0058939 A1 | 5/2002 | Wagner et al. |
| 2003/0187440 A1 | 10/2003 | Richelsoph et al. |
| 2004/0030339 A1 | 2/2004 | Wack et al. |
| 2004/0097935 A1 | 5/2004 | Richelsoph et al. |
| 2004/0102776 A1 | 5/2004 | Huebner |
| 2004/0127896 A1 | 7/2004 | Lombardo et al. |
| 2004/0254579 A1* | 12/2004 | Buhren .............. A61B 17/8033 606/71 |
| 2004/0267261 A1* | 12/2004 | Derouet .............. A61B 17/8047 606/70 |
| 2005/0015131 A1* | 1/2005 | Fourcault .......... A61B 17/7059 607/116 |
| 2005/0027296 A1 | 2/2005 | Thramann et al. |
| 2005/0043736 A1* | 2/2005 | Mathieu .............. A61B 17/8047 606/288 |
| 2005/0049594 A1 | 3/2005 | Wack et al. |
| 2005/0154392 A1* | 7/2005 | Medoff .............. A61B 17/8047 606/287 |
| 2005/0187552 A1 | 8/2005 | Michelson |
| 2005/0240187 A1 | 10/2005 | Huebner et al. |
| 2007/0043366 A1 | 2/2007 | Pfefferle et al. |
| 2007/0123879 A1* | 5/2007 | Songer .............. A61B 17/8033 606/288 |
| 2008/0103501 A1 | 5/2008 | Ralph et al. |
| 2008/0306550 A1* | 12/2008 | Matityahu .......... A61B 17/1728 606/290 |
| 2009/0076554 A1 | 3/2009 | Huebner et al. |
| 2009/0088807 A1* | 4/2009 | Castaneda .......... A61B 17/8047 606/286 |
| 2009/0192549 A1* | 7/2009 | Sanders ............. A61B 17/7059 606/280 |
| 2009/0248087 A1 | 10/2009 | Lewis et al. |
| 2009/0275987 A1 | 11/2009 | Graham et al. |
| 2010/0256686 A1* | 10/2010 | Fisher ................ A61B 17/8047 606/286 |
| 2010/0262194 A1 | 10/2010 | Wagner et al. |
| 2011/0112584 A1 | 5/2011 | Frigg |
| 2012/0226321 A1 | 9/2012 | Gonzalez-Hernandez |
| 2012/0303071 A1* | 11/2012 | Black ................ A61B 17/8047 606/305 |
| 2013/0041375 A1 | 2/2013 | Fierlbeck et al. |
| 2013/0060251 A1 | 3/2013 | Eglseder, Jr. |
| 2013/0204300 A1 | 8/2013 | Michelson |

(56) References Cited

U.S. PATENT DOCUMENTS

| | | |
|---|---|---|
| 2013/0211461 A1 | 8/2013 | Christen |
| 2013/0274813 A1 | 10/2013 | Mathieu et al. |
| 2013/0304132 A1* | 11/2013 | Heilman ............ A61B 17/8047 606/281 |
| 2013/0345760 A1 | 12/2013 | Lombardo et al. |
| 2014/0148861 A1 | 5/2014 | Simon et al. |
| 2014/0222084 A1 | 8/2014 | Fritzinger et al. |
| 2014/0228895 A1 | 8/2014 | Ziolo et al. |
| 2014/0367268 A1 | 12/2014 | Naito et al. |
| 2015/0305877 A1 | 10/2015 | Gargac et al. |
| 2016/0038199 A1 | 2/2016 | Wiederkehr et al. |
| 2016/0310181 A1 | 10/2016 | Frigg |

FOREIGN PATENT DOCUMENTS

| | | |
|---|---|---|
| FR | 2 674 118 A1 | 9/1992 |
| FR | 2 739 151 A1 | 3/1997 |
| FR | 2 744 011 A1 | 8/1997 |
| FR | 2 790 198 A1 | 9/2000 |
| FR | 2792185 A1 | 10/2000 |
| FR | 2844702 A1 | 3/2004 |
| SU | 1130332 A1 | 12/1984 |
| SU | 1223901 A1 | 4/1986 |
| WO | 8201645 A1 | 5/1982 |
| WO | 9407040 A1 | 3/1994 |
| WO | 99/09903 A1 | 3/1999 |

\* cited by examiner

FLOATING LOCKING INSERT

FIELD OF THE INVENTION

The present invention relates generally to attachment devices for connecting a plate to a support, such as a bone mass, and in particular relates to such devices that use polyaxial locking fasteners for fixation.

BACKGROUND OF THE INVENTION

Plates for osteosynthesis or arthrodesis are often fixed to bone substantially parallel to a longitudinal bone axis using screws or other fixation elements. Such plates are firmly fixed to a plurality of bone parts or fragments to prevent their movement relative to each other.

Spherical-head screws cooperating with radiused apertures in plates have been used to bring the plate into compression onto a bone until the friction of the plate on the bone stabilizes the assembly. These assemblies allow screws to be implanted during a surgical operation within the plate aperture at multiple angles relative to the plate to compress separated bone parts or fragments. The shortcoming of these systems is their low resistance to compression stresses exerted parallel to a plane generally defined by the plate.

A second generation of assembled screw-and-plate systems called monoaxial-locking and polyaxial-locking systems have relied on a threaded engagement of a screwhead with a plate aperture such that the strength of the assembly no longer depends on the compression of the plate against the bone. These systems allow for the assembly to take place away from the bone section being repaired and, in some instances, the possibility of selecting an angle of screw implantation during an operation while achieving strength sufficient for postoperative stresses.

Inserts have been added to monoaxial or polyaxial screw-and-plate systems in which the insert has a threaded engagement with any of the plate and the screw. In some such systems, a screw has been threaded into an insert to lock the insert, by way of friction, to a plate at an angle corresponding to a desired angle of implantation for the screw. To enhance the locking of these inserts, an outer surface of inserts has been given radial offsets. Such offsets have extended along an entire arcuate surface within a plane through a longitudinal axis defined by the inserts which creates friction that diminishes the control of the insert when attempting to set the desired insertion angle.

Thus, there exists a need for a better way in which to align fasteners for fixation within plates.

BRIEF SUMMARY OF THE INVENTION

In accordance with an aspect, an insert may include a body and a collar. The insert may be received within a plate aperture which may have an inner wall along at least a portion of the plate aperture.

The body may have inner and outer surfaces. The inner surface may define an insert aperture which may have a longitudinal axis. The collar may extend from a portion of the outer surface of the body in a first radial direction perpendicular to the longitudinal axis. The collar also may extend along only a portion of the outer surface of the body in a second radial direction transverse to the first radial direction and the longitudinal axis. The collar may define a first radial distance from the longitudinal axis at a first position of the collar and a second radial distance from the longitudinal axis at a second position of the collar that differs from the first radial distance.

In some arrangements, the collar may be a plurality of collars.

In some arrangements, the collar may include a plurality of sections. The plurality of sections may be spaced apart around the circumference of the body.

In some arrangements, an outer edge of each of the sections may define a respective first radial distance from the longitudinal axis at a first position of the respective outer edge and a respective second radial distance from the longitudinal axis at a second position of the respective outer edge that differs from the respective first radial distance.

In some arrangements, each of the plurality of sections may include three collar segments. An outer edge of a first collar segment may have a first radius along the outer edge of the first collar segment. A first end of an outer edge of a second collar segment may intersect the outer edge of the first collar segment. The outer edge of the second collar segment may have a second radius along the outer edge of the second collar segment. An outer edge of a third collar segment may intersect a second end of the outer edge of the second collar segment opposite the first end of the outer edge of the second collar segment. The outer edge of the third collar segment may have a third radius along the outer edge of the third collar segment. The third radius may be greater than the second radius. The second radius may be greater than the first radius.

In some arrangements, the collar may define a substantially non-circular shape with rounded corners.

In some arrangements, the collar may have a maximum length defined by a first linear distance in a direction perpendicular to the longitudinal axis from the outer surface of the body to an edge of the collar. The collar also may have a maximum width defined by a second linear distance in a direction parallel to the longitudinal axis. The first linear distance may be less than the second linear distance.

In some arrangements, the collar may have a maximum length defined by a first linear distance in a direction perpendicular to the longitudinal axis from the outer surface of the body to an edge of the collar. The collar also may have a maximum width defined by a second linear distance in a direction parallel to the longitudinal axis. The first linear distance may be greater than the second linear distance.

In some arrangements, the collar may have opposing upper and lower stopper surfaces. The upper and lower stopper surfaces may be configured for contacting corresponding upper and lower stopper surfaces of the plate.

In some arrangements, the upper and lower stopper surfaces of the collar may intersect. In this manner, the upper and lower stopper surfaces may define an edge. The edge may be configured for contacting the inner wall.

In some arrangements, each of the upper and lower stopper surfaces of the collar may intersect an edge surface to define opposing upper and lower edges. The upper and lower edges may be configured for contacting the inner wall.

In some arrangements, the edge surface may be concave.

In some arrangements, the insert aperture may be threaded for receipt of a threaded fastener.

In some arrangements, the inner surface may include at least one relief section. Any of the relief sections may define a plurality of separated thread sections.

In some arrangements, the body may include a slot that may extend through the inner and outer surfaces. The body may be compressible between rest and compressed conditions such that the slot may have a greater width in the rest condition than the slot has in the compressed condition.

In some arrangements, the body may include a plurality of notches that may extend into a thickness of the body defined by the inner and outer surfaces. The plurality of notches may be configured for receiving tines of an instrument. At least first and second notches of the plurality of notches may be positioned on opposite sides of the slot and may be moveable relative to each other. In this manner, when the first and second notches are moved in a direction toward each other, the body may be compressed and the slot width may be become smaller.

In accordance with another aspect, a fixation system may include a plate and an insert. The plate may have at least one plate aperture which may have an inner wall along at least a portion of the plate aperture.

The insert may include a body and a collar. The body may have inner and outer surfaces. The inner surface may define an insert aperture which may have a longitudinal axis. The collar may extend from a portion of the outer surface of the body in a first radial direction perpendicular to the longitudinal axis. The collar also may extend along only a portion of the outer surface of the body in a second radial direction transverse to the first radial direction and the longitudinal axis. The collar may define a first radial distance from the longitudinal axis at a first position of the collar and a second radial distance from the longitudinal axis at a second position of the collar that differs from the first radial distance. The insert may be receivable within the plate aperture of the plate. In this manner, the collar may contact and may be slideable along the inner wall of the plate.

In some arrangements, the collar may be a plurality of collars.

In some arrangements, the inner wall may define a longitudinal axis. The insert may be rotatable about the longitudinal axis of the inner wall and may be translatable along the longitudinal axis of the inner wall.

In accordance with another aspect, a fixation system may include a plate and an insert. The plate may have at least one plate aperture which may have an inner wall defining an inner wall longitudinal axis and may have a guidance surface that may extend from the inner wall. The inner wall may define a wall aperture defined by a first radius, and the guidance surface may be defined by a second radius smaller than the first radius defining the wall aperture.

The insert may be receivable in the inner wall of the plate and may be rotatable about rotational axes perpendicular to the inner wall longitudinal axis. An outer surface of the insert may be curved such that the insert may be slideable along the guidance surface during rotation of the insert about the rotational axes.

In some arrangements, the guidance surface may be a plurality of guidance surfaces.

In some arrangements, the insert may define a longitudinal axis and may include a collar. The collar may extend from a portion of the outer surface of the insert in a first radial direction perpendicular to the insert longitudinal axis and may extend along only a portion of the outer surface of the insert in a second radial direction transverse to the first radial direction and the insert longitudinal axis. The collar may define a first radial distance from the insert longitudinal axis at a first position of the collar and a second radial distance from the insert longitudinal axis at a second position of the collar that differs from the first radial distance. The collar may be slideable along the inner wall during rotation of the insert about the rotational axes.

In some arrangements, the collar may be a plurality of collars.

In accordance with another aspect, a fixation system may include a plate and an insert. The plate may have at least one plate aperture which may have an inner wall defining an inner wall longitudinal axis and may have upper and lower plate end surfaces extending from the inner wall.

The insert may be receivable in the inner wall of the plate and may be rotatable about rotational axes perpendicular to the inner wall longitudinal axis. The insert may define a longitudinal axis and may include a collar. The collar may extend from a portion of the outer surface of the insert in a first radial direction perpendicular to the insert longitudinal axis and may extend along only a portion of the outer surface of the insert in a second radial direction transverse to the first radial direction and the insert longitudinal axis. The collar may have opposing upper and lower stopper surfaces. In this manner, the upper plate end surface of the plate may prevent rotation of the upper stopper surface of the collar, and the lower plate end surface of the plate may prevent rotation of the lower stopper surface of the collar.

In accordance with another aspect, a plate may be fixed to a bone by a process. In particular, an insert may be received in a plate aperture of a plate defining a plate longitudinal axis. The insert may include a body and a collar. The body may have inner and outer surfaces. The inner surface of the body may define a body aperture through the inner surface defining an insert longitudinal axis. The collar may extend from the body in a first radial direction perpendicular to the insert longitudinal axis and may extend along only a portion of the body in a second radial direction transverse to the first radial direction and the insert longitudinal axis. The collar may define a first radial distance from the insert longitudinal axis at a first position of the collar and a second radial distance from the insert longitudinal axis at a second position of the collar that differs from the first radial distance. A fastener may be threaded into the inner surface of the insert at a predetermined angle relative to the plate longitudinal axis. The insert may be rotated to compress the insert to lock the fastener at the predetermined angle.

DETAILED DESCRIPTION

Figure 1:
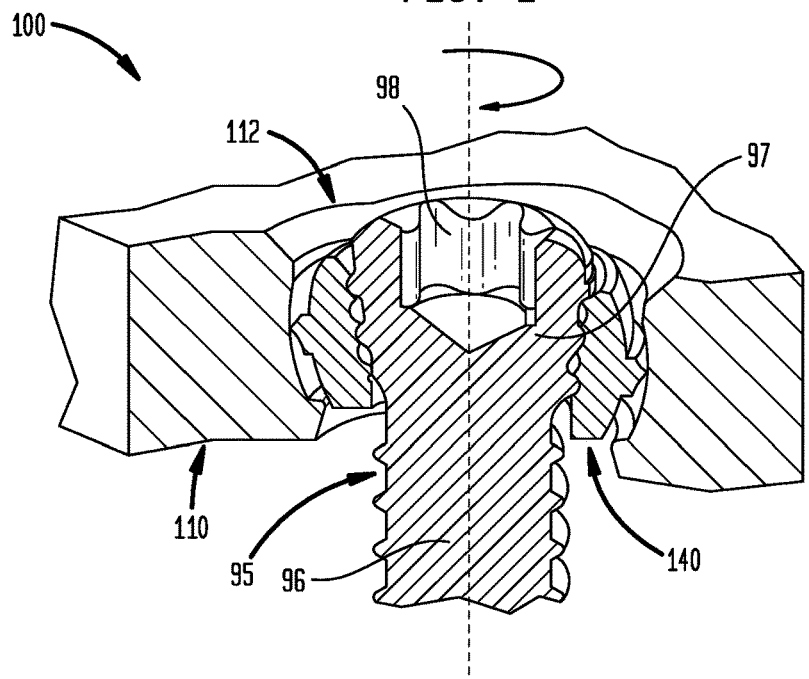
FIG. 1 is a perspective cross-sectional view of a fixation system in accordance with an embodiment.

Referring now to the drawings, as shown in FIG. 1, fixation system 100 generally includes plate 110, insert 140, and fastener 95. Plate 110 may be but is not limited to being a bone fixation plate, such as may be used for the treatment of proximal humeral, radial, elbow, or clavicle fractures. Plate 110 may be but is not limited to being made of biocompatible materials such as titanium and its alloys, cobalt and its alloys including cobalt-chromium, and stainless steel. Insert 140 may be dimensioned and may be flexible such that the insert may be received for polyaxial movement within and frictional locking with aperture 112 of plate 110. Insert 140 may be but is not limited to being made of biocompatible materials such as titanium and its alloys, cobalt and its alloys including cobalt-chromium, and stainless steel. Fastener 95 may be a locking screw having a fully threaded shank 96, which may be received into a patient's bone or other tissue, as well as threaded head 97 which may include bore 98 for receipt of a turning tool such as a hex-head or TORX screwdriver. As shown, head 97 of fastener 95 may be tapered such that a perimeter of the head adjacent shank 96 may be smaller than a perimeter of the head surrounding bore 98.

Figure 2:
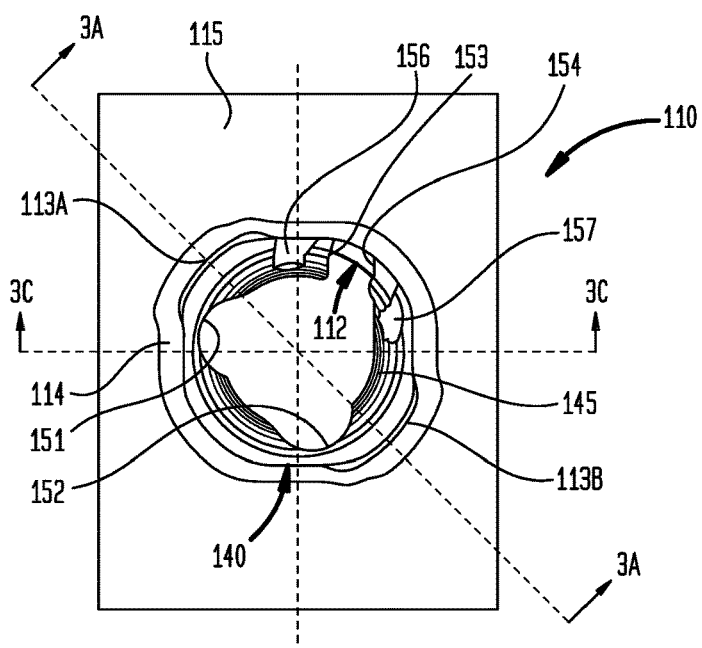
FIG. 2 is a plan view of a section of a plate and an insert of the fixation system of FIG. 1.

As shown in FIG. 2, plate aperture 112 of plate 110 may pass through a thickness of plate 110 and may be generally in a square form with the exception of two grooves 113A, 113B at opposing corners at a top end of the aperture. Upper chamfer 114 may extend around plate aperture 112 and between the plate aperture and top surface 115 of plate 110. Grooves 113A, 113B and upper chamfer 114 ease the assembly of insert 140 into plate 110.

As shown in FIGS. 3A-3D, plate aperture 112 may include inner wall 120 as well as opposing upper and lower plate end surfaces 122, 123 intersecting and extending transversely to opposing ends of inner wall 120 to provide opposing abutments. As in the arrangement shown, inner wall 120, which may have a substantially smooth surface, may extend along a majority of plate aperture 112. Inner wall 120 may have a cross-section defined by any given plane through a longitudinal axis of aperture 112 that is substantially in the form of a truncated ellipse. Plate aperture 112 may include upper guidance surface 126 intersecting upper plate end surface 122 on one end and chamfer 114 on an opposite end of the upper guidance surface to form an upper bearing surface for insert 140 as well as lower guidance surface 127 intersecting lower plate end surface 123 on one end and lower chamfer 116, which extends to bottom surface 125 of plate 110, on an opposite end to form a lower bearing surface for insert 140.

As further shown, insert 140 may include a body or inner body 142 and collar 162. Inner body 142 may include inner surface 144 and outer surface 146 separated by a thickness of the inner body. Inner and outer surfaces 144, 146 of insert 140 may extend between top surface 148 and bottom surface 149 of the inner body. As in the example shown, outer surface 146 may be substantially smooth and generally may be in the form of a truncated hollow ellipsoid such that cross-sections of the outer surface taken through the longitudinal axis of aperture 112 define truncated ellipses. In the example shown, outer surface 146 is in the form of a truncated hollow sphere.

Inner surface 144 may include threads 145 extending along a majority of the length of the inner surface. Inner surface 144 may be tapered such that a portion of the inner surface intersecting top surface 148 may have a larger perimeter than a portion of the inner surface intersecting bottom surface 149. In this manner, inner surface 144 may be threadably engaged with head 97 of fastener 95.

As best shown in FIG. 2, inner surface 144 may include first and second recesses 151, 152 situated generally opposite a slot defined by opposing insert ends 153, 154 and extending through the thickness of inner body 142 in which first recess 151 is closer to the slot. In this manner, insert 140 may be compressed from a rest condition in which the slot and the insert have preset rest widths to a compressed condition in which the slot and the insert have widths smaller than their respective preset rest widths. As in the example shown, opposing insert ends 153, 154 of insert 140 may be aligned such that when insert 140 is compressed sufficiently, opposing insert ends 153, 154 may abut each other. To facilitate the compression of insert 140, inner body 142 may include notches 156, 157 adjacent to insert ends 153, 154. Notches 156, 157 may be dimensioned to receive tines of tongs, a snap ring insertion tool, or other suitable instrument which may be used to urge insert ends 153, 154 toward each other to reduce the width of insert 140 for placement into plate aperture 112 of plate 110.

Figure 3A:
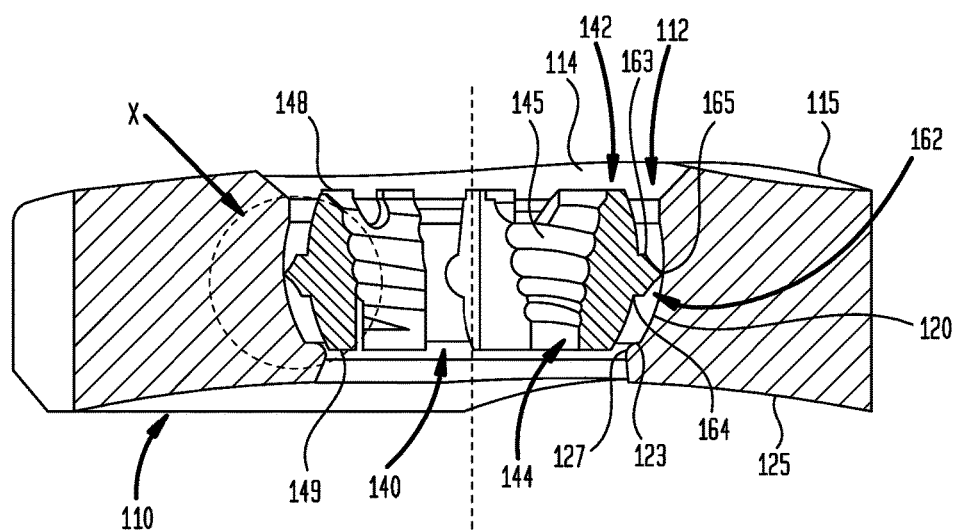
FIG. 3A is an elevation view of a cross-section taken at 3A-3A of a portion of the plate and the insert of FIG. 2.
Figure 3B:
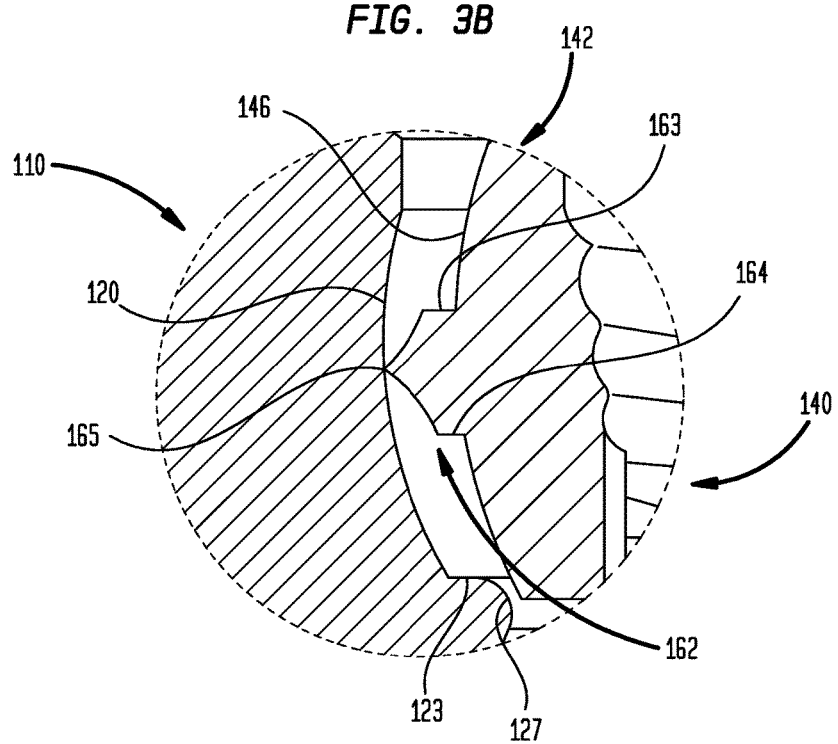
FIG. 3B is an exploded view taken at region X of FIG. 3A.
Figure 3C:
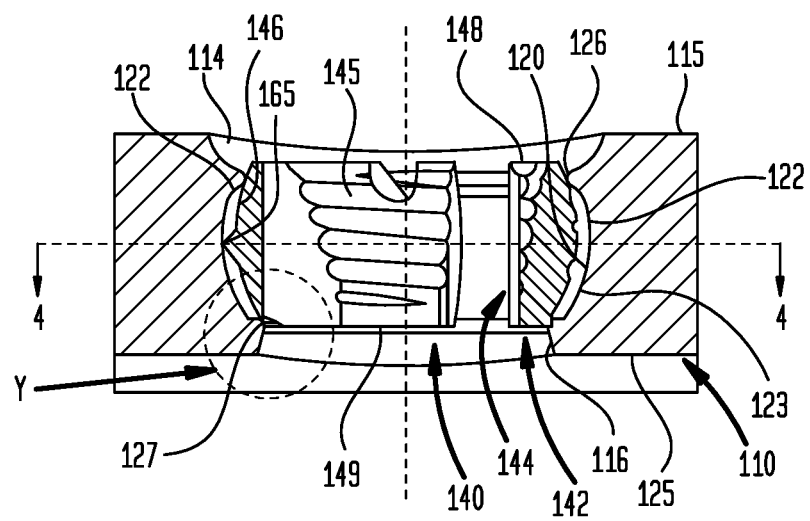
FIG. 3C is an elevation view of a cross-section taken at 3C-3C of a portion of the plate and the insert of FIG. 2.
Figure 3D:
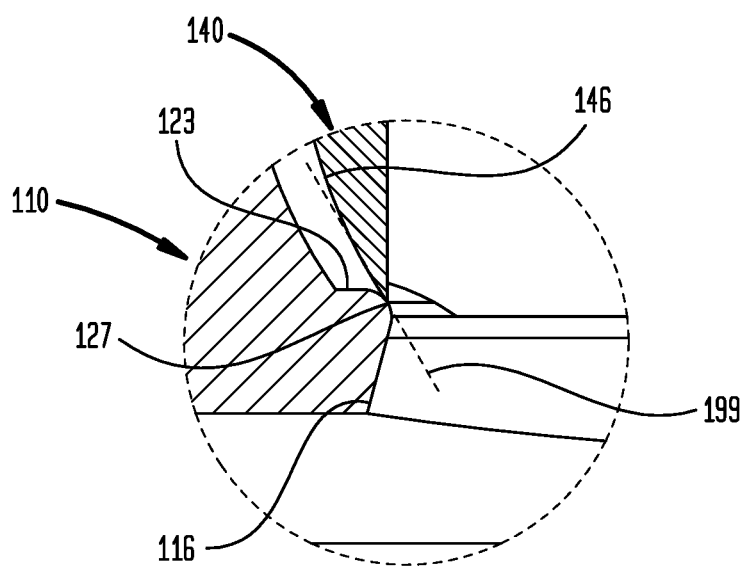
FIG. 3D is an exploded view taken at region Y of FIG. 3C.

Referring to FIGS. 2, 3A, and 3C, collar 162 extends along the entire perimeter of outer surface 146 of inner body 142 and covers a generally central portion of the outer surface of the inner body. During compression of insert 140 such that opposing insert ends 153, 154 are brought closer together, a section of collar 162 adjacent to the slot defined by insert ends 153, 154 may be generally the shortest distance from a longitudinal axis through a centroid of the insert relative to the rest of the collar. As such, plate aperture 112 and plate grooves 113A, 113B may be dimensioned such that collar 162 and thus insert 140 must be oriented such that the slot defined by insert ends 153, 154 is within a region of plate 110 between plate grooves 113A, 113B during insertion of the insert into the plate. Likewise, once insert 140 is placed within plate 110, the insert may be removed only when the insert is oriented about the longitudinal axis of aperture 112 in which the slot defined by insert ends 153, 154 is situated between plate grooves 113A, 113B.

As shown in FIGS. 3A-3D, collar 162 includes opposing upper stopper surface 163 and lower stopper surface 164. Upper and lower stopper surfaces 163, 164 extend from inner body 142 such that, during rotation of insert 140 within a plane passing through the longitudinal axis of plate aperture 112, i.e., during vertical rotation of the insert, when the insert is within the plate, the upper and lower stopper surfaces may abut either or both of corresponding upper and lower plate end surfaces 122, 123. In this manner, upper and lower plate end surfaces 122, 123 restrict vertical rotation of the insert within the plate and aid in preventing disassembly of the insert from the plate. As in the example shown, the entirety of insert 140 may be moveable in a vertical direction along the longitudinal axis of plate aperture 112 when upper and lower stopper surfaces 163, 164 are between upper and lower plate end surfaces 122, 123. Upper and lower plate end surfaces 122, 123 are located along plate aperture 112 such that insert 140 may be rotatable up to 15 degrees in clockwise and counterclockwise directions in which maximum travel is possible when collar 162 is centered in the vertical direction along inner wall 120 of plate 110.

Upper and lower stopper surfaces 163, 164 may intersect to define edge 165. When insert 140 is oriented in plate 110 such that the slot defined by insert ends 153, 154 of insert 140 is situated between plate grooves 113A, 113B as illustrated in FIG. 2, edge 165 may be in contact with inner wall 120 in the cross-section shown in FIG. 3A and may be in contact with only one side of the inner wall in the cross-section shown in FIG. 3C.

Still referring to FIGS. 3A-3D, when the slot defined by insert ends 153, 154 of insert 140 is situated between plate grooves 113A, 113B as illustrated in FIG. 2, radii defining the cross-section of outer surface 146 of inner body 142 shown in FIG. 3A may be different than radii defining the cross-section of inner wall 120 such that the cross-section of outer surface 146 shown curves away from the cross-section of inner wall 120 shown and inwardly towards the longitudinal axis of aperture 112 of plate 110. As such, portions of outer surface 146 nearest top and bottom surfaces 148, 149 of inner body 142 in the cross-section shown in FIG. 3A are further from inner wall 120 than portions of outer surface 146 further away from the top and bottom surfaces of the inner body in the cross-section shown in FIG. 3A. In contrast, when insert 140 is in this same orientation, radii defining the cross-section of outer surface 146 of inner body 142 shown in FIG. 3C may be different than radii defining the cross-section of inner wall 120 such that the cross-section of outer surface 146 shown curves only slightly inwardly towards the longitudinal axis of aperture 112 of plate 110. As such, portions of outer surface 146 nearest top and bottom surfaces 148, 149 of inner body 142 in the cross-section shown in FIG. 3C are further from inner wall 120 than portions of outer surface 146 further away from the top and bottom surfaces of the inner body in the cross-section shown in FIG. 3C.

When insert 140 is in the orientation shown in FIGS. 3A-3D, the cross-section of outer surface 146 shown in FIG. 3C near the intersections of the outer surface with each of top and bottom surfaces 148, 149 may abut the respective upper and lower guidance surfaces 126, 127 of plate aperture 112 of plate 110 on the side opposite where edge 165 of the insert contacts inner wall 120 in the cross-section shown in FIG. 3C. Similarly, the cross-section of outer surface 146 shown in FIG. 3C near the intersection of the outer surface with the top surface 148 may abut the upper guidance surface 126 of aperture 112 of plate 110 on the same side that edge 165 of the insert contacts inner wall 120 in the cross-section shown in FIG. 3C. As demonstrated by the imaginary line of contact 199 shown in FIG. 3D, upon rotation of insert 140 from the orientation of the insert shown in FIGS. 3A-3D within a plane passing through the longitudinal axis of plate aperture 112, the cross-section of outer surface 146 on the same side which edge 165 contacts inner wall 120 will contact lower guidance surface 127. In this manner, outer surface 146 and thus insert 140 is further guided by upper and lower guidance surfaces 126, 127 of plate 110 during such rotation.

As in the example of FIGS. 3A-3D, contact between upper and lower guidance surfaces 126, 127 of plate aperture 112 of plate 110 and outer surface 146 of insert 140 may be substantially a point contact. Similarly, contact between inner wall 120 and edge 165 of collar 162 of insert 140 may be substantially a point or line contact. In this manner, friction between plate 110 and insert 140 may be minimized during rotation of the insert about the longitudinal axis of plate aperture 112 of the plate and during rotation of the insert within planes passing through the longitudinal axis of aperture 112.

Figure 4:
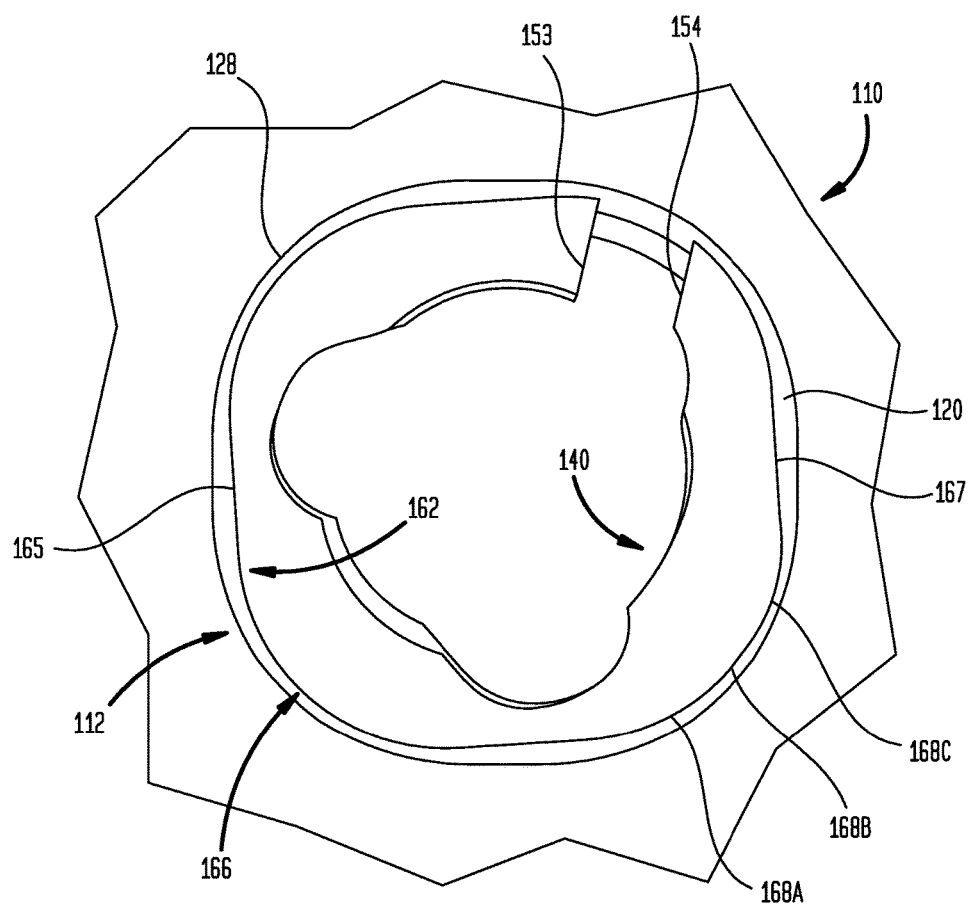
FIG. 4 is a plan view of a cross-section taken at 4-4 of FIG. 3A.

Referring now to FIG. 4, along a central section of plate aperture 112 of plate 110, inner wall 120 of the plate aperture may be in the form of a square having rounded corners 128. Likewise, along a central section of insert 140, the insert may be substantially in the form of a square having collar sections 166 in the form of rounded corners defined by edge 165 of collar 162 in which the rounded corners of the insert generally correspond to the rounded corners of the plate when the insert is placed into the plate. As shown, one of collar sections 166 of collar 162 may be divided by the slot defined by insert ends 153, 154. Each of collar sections 166 may be separated by recesses 167 of collar 162 which, when insert 140 is fully inserted into plate 110, do not contact aperture 112 of the plate. In this manner, when fastener 95 is inserted, such as by threading, into insert 140, the interface of collar sections 166 of the insert with respective rounded corners 128 may provide fixation of the insert to the plate and thus fixation of the fastener relative to the plate. Collar recesses 167 may also provide for greater flexibility of insert 140 due to the decrease in thickness of the insert at the locations of these recesses.

Each of collar sections 166 of collar 162 of insert 140 may include a plurality of collar segments, such as first collar segment 168A, second collar segment 168B having an end intersecting an end of the first collar segment, and third collar segment 168C intersecting an end of the second collar segment opposite the end of the second collar segment 168B intersecting the first collar segment. As demonstrated in the example shown in FIG. 4, the points along the length of first collar segment 168A may be set at a distance from a longitudinal axis of insert 140 that is less than the distance that the points along the length of collar segment 168B are set at a distance from the longitudinal axis of the insert, and the points along the length of collar segment 168B may be set at a distance from the longitudinal axis of the insert that is less than the distance that the points along the length of collar segment 168C are set at a distance from the longitudinal axis of the insert. In this manner, upon insertion of insert 140 into plate aperture 112 of plate 110 and engagement of head 97 of fastener 95 with inner surface 144 of insert 140, rotation of insert 140 about the longitudinal axis of plate 140 in a clockwise direction may produce an increasing amount of friction between collar 162 of the insert and inner wall 120 of the plate until the insert becomes locked in position within the plate aperture. In the example shown, collar 162 of insert 140 may be made of a material that is as hard or harder than the material of aperture 112 of plate 110 such that the collar does not deform upon locking within the plate aperture. In arrangements in which aperture 112 of plate 110 has a similar hardness collar 162 of insert 140, plate aperture 112 also may not deform during vertical movement of collar 162 along the plate aperture. In other such arrangements, collar 162 of insert 140 may be made of a harder material than aperture 112 of plate 110 such that the collar may carve or otherwise deform the plate to create rigid fixation between the insert and the plate. In such other arrangements, the section of collar 162 adjacent to the slot defined by insert ends 153, 154 may be generally the shortest distance from the longitudinal axis through the centroid of the insert relative to the rest of the collar.

In some arrangements, head 97 of fastener 95 may be locked with insert 140 at the same time the insert is locked with plate aperture 112, or as in the example shown, continued rotation of the fastener may lock the fastener head. In the example shown, head 97 of fastener 95 may be inserted into inner surface 144 of insert 140, and shank 96 of fastener 95 may be inserted into a bone, at a predetermined angle relative to the longitudinal axis of aperture 112 of plate 110. In this manner, upon locking of insert 140 within plate aperture 112 and locking of fastener 95 with inner surface 144 of the insert, the insert and the fastener may be locked at the predetermined angle relative to the longitudinal axis of the plate aperture of plate 110.

During a surgical operation, a physician, or other qualified medical professional, may determine that a set of bone fragments or bone parts require repair by way of an osteosynthesis or arthrodesis procedure using plate 110. Plate 110 may be placed onto each of the bone fragments or bone parts such that at least one plate aperture 112 lies on each of the bone fragments or bone parts. Insert 140 may be inserted into inner wall 120 of a plate aperture 112 selected by the medical professional. The medical professional may determine an appropriate insertion angle for insertion of fastener 95 into a bone fragment or bone part to achieve sufficient, and preferably optimal, postoperative stresses. Shank 96 of fastener 95 may be inserted through inner surface 144 of insert 140 to orient the insert. Fastener shank 96 then may be threaded, such as by a TORX or a hex head screwdriver, into the bone fragment or bone part at the predetermined insertion angle. As fastener shank 96 is threaded further into the bone fragment or bone part, fastener head 97 may be threaded into threads 145 of inner surface 144 of insert 140 causing rotation of the insert within plate 110 until the insert becomes locked within plate aperture 112. In this manner, fastener 95 may be locked with insert 140 and locked relative to plate aperture 112 of plate 110, at the predetermined angle. If the medical professional is unsatisfied with the insertion angle of fastener 95, fastener 95 may be unthreaded from the bone fragment or bone part, preferably prior to threading of head 97 with insert 140, and a new insertion angle for the fastener may be selected. Fastener 95 then may be inserted into the bone fragment or bone part at the newly selected orientation and locked relative to plate 110 as described previously herein.

Figure 5:
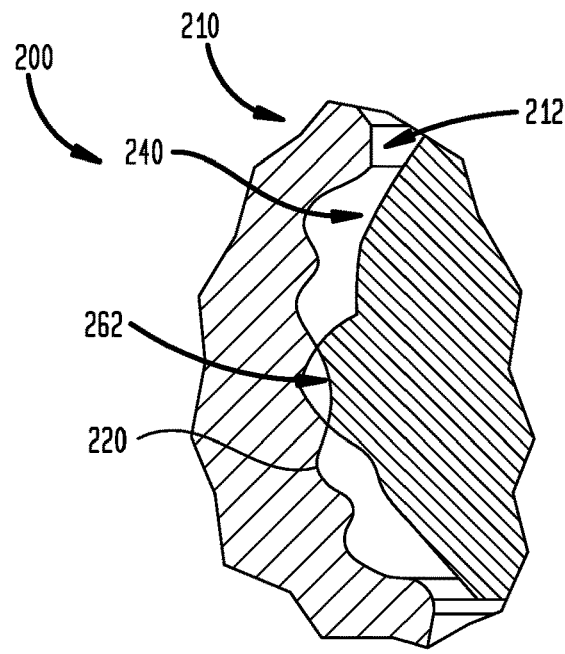
FIG. 5 is an elevation cross-sectional view of portions of a plate and an insert in accordance with another embodiment.

As shown in FIG. 5, in an alternative arrangement, fixation system 200 may be the same as fixation system 100 with the exception that fixation system 200 may include plate 210 including plate aperture 212 having inner wall 220 in place of plate aperture 112 and inner wall 120, respectively, of plate 110 and insert 240 having collar 262 in place of collar 162 of insert 140. Insert 240 may be the same as insert 140 with the exception that at least collar 262 of insert 240, and in some arrangements all of insert 240, is made of a softer material than plate 210. For example, insert 240 may be made of but is not limited to being made of any of cobalt-chromium alloys, titanium alloys, steel and its alloys, medical grade polymers, and ceramic when plate 210 is made of a relatively harder material. As such, vertical movement of collar 262 against inner wall 220 deforms the inner wall. In this manner, insert 240 is maintained in plate aperture 212 by both the deformed surface of inner wall 220 and the compression of the insert against the inner wall upon receipt of a fastener into the insert.

Figure 6:
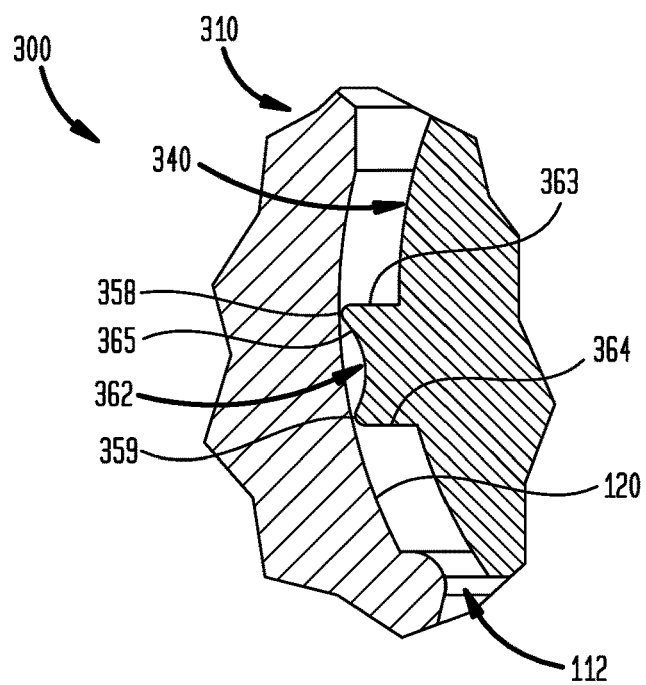
FIG. 6 is an elevation cross-sectional view of portions of a plate and an insert in accordance with another embodiment.

As shown in FIG. 6, in an alternative arrangement, fixation system 300 may be the same as fixation system 100 with the exception that fixation system 300 may include insert 340 having collar 362 in place of collar 162 of insert 140. Collar 362 may be the same as collar 162 with the exception that collar 362 may include upper and lower stopper surfaces 363, 364 in place of upper and lower stopper surfaces 163, 164 and may include edge surface 365 which intersects upper and lower stopper surfaces 363, 364 to define edges 358, 359. As shown, edge surface 365 may be concave such that upper edge 358 and lower edge 359 contact inner wall 120 of plate 110 during rotation and vertical movement of insert 340 within plate aperture 112.

In some alternative arrangements, the relative distances of any of the collar segments may be in any mixed order and, in some arrangements, may be the same distance such that there are only two segments in any collar section of an insert. In some alternative arrangements, the plate aperture and the insert may be in different corresponding non-circular forms at their central cross-sections along the longitudinal axis, such as but not limited to a triangular or an elliptical form, rather than in the square forms of plate 110 and insert 140.

It is to be understood that the disclosure set forth herein includes all possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the invention, and in the invention generally.

Furthermore, although the embodiments disclosed herein have been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the claims below. Moreover, the foregoing disclosure should be taken by way of illustration rather than by way of limitation as the present invention is defined by the claims set forth below.

The invention claimed is:

1. An insert for receipt within a plate aperture having an inner wall along at least a portion thereof, comprising:
 a body having inner and outer surfaces, the inner surface defining an insert aperture having a longitudinal axis; and
 a collar extending from a portion of the outer surface of the body in a first radial direction within a first plane perpendicular to the longitudinal axis and extending along only a central portion of the outer surface of the body in a second radial direction transverse to the first radial direction and the longitudinal axis,
 wherein the collar includes a first curved section having a first outer edge that defines a first radius within the first plane and a second curved section having a second outer edge that defines a second radius within the first plane that differs from the first radius.

2. The insert of claim 1, wherein the collar includes an additional curved section spaced apart in the first plane from the first and the second curved sections around a perimeter of the body.

3. The insert of claim 2, wherein the first curved section defines a first distance from the longitudinal axis to a first position of the first outer edge within the first plane and the second curved section defines a second distance from the longitudinal axis to a second position of the second outer edge within the first plane that differs from the first distance.

4. The insert of claim 3, wherein each of the curved sections includes first, second, and third collar segments, wherein the first collar segment defines the first radius in the first plane along the respective outer edge of each of the respective curved sections, the second collar segment has a first end intersecting the first collar segment in the first plane and defines a radius within the first plane along the respective outer edge of each of the respective curved sections, and the third collar segment intersects a second end of the second collar segment opposite the first end of the second collar segment and defines a radius within the first plane along the respective outer edge of each of the respective curved sections, wherein the third radius is greater than the second radius which is greater than the first radius.

5. The insert of claim 1, wherein the collar defines a substantially non-circular shape with rounded corners within the first plane.

6. The insert of claim 1, wherein the collar has a maximum length defined by a first linear distance in a direction perpendicular to the longitudinal axis from the outer surface of the body to an edge of the collar and a maximum width defined by a second linear distance in a direction parallel to the longitudinal axis, wherein the first linear distance is less than the second linear distance.

7. The insert of claim 1, wherein the collar has a maximum length defined by a first linear distance in a direction perpendicular to the longitudinal axis from the outer surface of the body to an edge of the collar and a maximum width defined by a second linear distance in a direction parallel to the longitudinal axis, wherein the first linear distance is greater than the second linear distance.

8. The insert of claim 1, wherein the collar has opposing upper and lower stopper surfaces configured for contacting corresponding upper and lower stopper surfaces of the plate.

9. The insert of claim 8, wherein the upper and lower stopper surfaces of the collar intersect to define an edge configured for contacting the inner wall.

10. The insert of claim 8, wherein each of the upper and lower stopper surfaces of the collar intersect an edge surface to define opposing upper and lower edges, the upper and lower edges configured for contacting the inner wall.

11. The insert of claim 10, wherein the edge surface is concave.

12. The insert of claim 1, wherein the insert aperture is threaded for receipt of a threaded fastener.

13. The insert of claim 12, wherein the inner surface includes at least one relief section defining a plurality of separated thread sections.

14. The insert of claim 1, wherein the body includes a slot extending through the inner and outer surfaces, and wherein the body is compressible between rest and compressed conditions such that the slot has a greater width in the rest condition than the slot has in the compressed condition.

15. The insert of claim 14, wherein the body includes a plurality of notches extending into a thickness thereof defined by the inner and outer surfaces, the plurality of notches being configured for receiving tines of an instrument, and wherein at least first and second notches of the plurality of notches are positioned on opposite sides of the slot and moveable relative to each other such that when the first and second notches are moved in a direction toward each other, the body compresses and the slot width becomes smaller.

16. A fixation system comprising:
A plate having at least one plate aperture having an inner wall along at least a portion thereof; and
the insert of claim 1, wherein the insert is receivable within the plate aperture of the plate such that the collar contacts and is slideable along the inner wall of the plate.

17. The fixation system of claim 16, wherein the inner wall defines a longitudinal axis, and wherein the insert is rotatable about the longitudinal axis of the inner wall and translatable along the longitudinal axis of the inner wall.

* * * * *